United States Patent [19]
Ringer et al.

[11] Patent Number: 5,973,148
[45] Date of Patent: Oct. 26, 1999

[54] N-ARYLSULFILIMINE COMPOUNDS AND THEIR USE AS CATALYSTS IN THE PREPARATION OF N-ARYLARYLSULFONAMIDE COMPOUNDS

[75] Inventors: James W. Ringer, Midland, Mich.; Carmen A. Scott, Redmond, Wash.; Douglas L. Pearson; Anne P. Wallin, both of Midland, Mich.

[73] Assignee: Dow AgroSciences LLC, Indianapolis, Ind.

[21] Appl. No.: 09/220,304

[22] Filed: Dec. 23, 1998

Related U.S. Application Data

[63] Continuation of application No. 08/970,132, Nov. 13, 1997.
[60] Provisional application No. 60/030,896, Nov. 13, 1996.

[51] Int. Cl.$^6$ ............ C07D 487/04; C07D 213/73; C07C 145/02
[52] U.S. Cl. ............ 544/263; 544/263; 564/440; 564/102; 546/119; 546/297; 546/304
[58] Field of Search ............ 544/263; 564/102, 564/440; 546/297, 304, 119

[56] References Cited

U.S. PATENT DOCUMENTS

| | | | |
|---|---|---|---|
| 4,496,765 | 1/1985 | Ku et al. ............ | 564/440 |
| 4,578,514 | 3/1986 | Getman ............ | 564/102 |
| 4,910,306 | 3/1990 | McKendry ............ | 544/263 |
| 5,163,995 | 11/1992 | Van Heertum et al. ............ | 71/92 |
| 5,177,206 | 1/1993 | Johnson et al. ............ | 544/263 |
| 5,201,938 | 4/1993 | Costales et al. ............ | 504/241 |
| 5,461,161 | 10/1995 | Arndt et al. ............ | 546/304 |
| 5,571,775 | 11/1996 | Van Heertum ............ | 504/246 |

FOREIGN PATENT DOCUMENTS 598396   5/1994   European Pat. Off. .

OTHER PUBLICATIONS

T. E. Varkey et al., *J. Org. Chem.*, 39, 3365–3372 (1974).
A. K. Sharma et al., *J. Org. Chem.*, 40, 2758–2765 (1974).
I. V. Koval, *Russian Chemical Reviews*, 59. 819–831 (1990) (in English).
T. L. Gilchrist et al. *Chemical Reviews*, 77, 409–435 (1976).
A. J. Mancuso et al., *Synthesis*, 1981, 165–185.
S. Shiraishi, et al., *Bulletin of the Chemical Society of Japan*, 56, 1514–1518 (1983).
Claus K. Peter et al. (J. Org. Chem. vol. 44, No. 16, (1979), pp. 2863–2871, 1979.

*Primary Examiner*—Jose' G. Dees
*Assistant Examiner*—Sabiha N Qazi
*Attorney, Agent, or Firm*—Craig E. Mixan; Donald R. Stuart; D. Wendell Osborne

[57] ABSTRACT

N-arylsulfilimine compounds, such as S,S-dimethyl-N-(2,6-dichlorophenyl)sulfilimine, were prepared and found to catalyze the reaction of aromatic sulfonyl chloride compounds, such as 2-chlorosulfonyl-7-fluoro-5-ethoxy[1,2,4]triazolo[1,5-c]pyrimidine, with aromatic amine compounds, such as 2,6-dichloroaniline, to form N-arylarylsulfonamide compounds, such as N-(2,6-dichlorophenyl)-7-fluoro-5-ethoxy[1,2,4]triazolo[1,5-c]-pyrimidine-2-sulfonamide. The aryl moiety of the N-arylsulfilimine catalyst and the aryl moiety of the aromatic amine compound were generally chosen to be identical.

20 Claims, No Drawings

N-ARYLSULFILIMINE COMPOUNDS AND THEIR USE AS CATALYSTS IN THE PREPARATION OF N-ARYLARYLSULFONAMIDE COMPOUNDS

CROSS-REFERENCE TO RELATED APPLICATIONS

This application is a continuation of U.S. application Ser. No. 08/970,132, filed Nov. 13, 1997, which claims the benefit of U.S. Provisional Application No. 60/030,896, filed Nov. 3, 1996.

BACKGROUND OF THE INVENTION

The present invention relates to the use of N-arylsulfilimine compounds as catalysts in the reaction of aromatic sulfonyl chloride compounds with aromatic amines to form N-arylarylsulfonamide compounds and to novel N-arylsulfilimine compounds.

The preparation of N-arylarylsulfonamide compounds by the reaction of aromatic sulfonyl chloride compounds with aromatic amine compounds typically gives unsatisfactory results because the reaction is slow and the yields are poor. The preparation of such compounds wherein the aromatic amine compound and/or the aromatic sulfonyl chloride compound possesses one or, especially, two ortho substituents is often particularly unsatisfactory because of the steric deactivation effect and, when the substituents are electron-withdrawing, the electronic deactivation effect of ortho substituents. Pyridine, picolines, and lutidines have long been known to catalyze the reaction of many sulfonyl chloride compounds with amines to form sulfonamides. Recently, it was reported that a mixture of a pyridine base and dimethyl sulfoxide gave improved results in many instances (U.S. Pat. No. 5,177,206). Many N-arylarylsulfonamide compounds are known in the art to be valuable herbicides and methods of obtaining them more readily and in improved yields are desirable.

A number of substituted N-phenylsulfilimine compounds are known, for example from *J. Org. Chem.*, 39, 3365–3372 (1974), and the preparation and some of the chemistry of these compounds has been reviewed in the literature, for example in *Russian Chemical Reviews*, 59, 819–831 (1990). Certain of these compounds have been reported to be useful intermediates for further synthesis. For example, rearrangement of such compounds having at least one unsubstituted ortho-position to obtain 2-alkylthiomethylaniline compounds has been reported in U.S. Pat. No. 4,496,765. The use of N-phenylsulfilimine compounds as catalysts for the preparation of sulfonamides has not been reported.

SUMMARY OF THE INVENTION

It has now been found that N-arylsulfilimine compounds catalyze the reaction of aromatic sulfonyl chloride compounds with aromatic amines to form N-arylarylsulfonamide compounds. The effect is especially significant in such reactions involving a relatively unreactive aromatic sulfonyl chloride compound and/or a relatively unreactive aromatic amine compound. Faster rates of reaction and improved yields are obtained.

The invention includes a process for the preparation of an N-arylarylsulfonamide compound of Formula IV:

Q-SO$_2$NH-AR wherein

Q and AR each independently represents an aromatic hydrocarbyl or aromatic heterocyclyl moiety which comprises combining a sulfonyl chloride compound of Formula II:

Q-SO$_2$Cl wherein Q is defined as above
with an amine compound of Formula III:

AR-NH$_2$ wherein AR is defined as above
in the presence of an aromatic tertiary amine base and an added catalytic amount of an N-arylsulfilimine compound of Formula I:

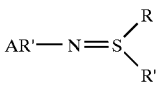

wherein
R represents methyl, ethyl, or n-propyl;
R' represents R, benzyl, or phenyl;
or R and R' together represent tetramethylene;
and AR' represents an aromatic hydrocarbyl or aromatic heterocyclyl moiety.

It is greatly preferred that AR' in the sulfilimine compound be selected to be identical with AR in the amine compound.

The preparation of an N-arylarylsulfonamide compound of Formula IV wherein AR represents a phenyl, pyridinyl, or 1-alkylpyrazolyl moiety optionally having 1 to 3 substituents selected from F, Cl, Br, I, NO$_2$, CN, O(C$_3$–C$_4$ alkenyl), or O(C$_3$–C$_4$ alkynyl); C$_1$–C$_4$ alkyl, O(C$_1$–C$_4$ alkyl), N(C$_1$–C$_4$ alkyl)$_2$, S(C$_1$–C$_4$ alkyl), SO$_2$(C$_1$–C$_4$ alkyl), CO$_2$(C$_1$–C$_4$ alkyl), CONH(C$_1$–C$_4$ alkyl), or CON(C$_1$–C$_4$ alkyl)$_2$ (each alkyl optionally mono to completely substituted with fluorine); or phenyl or phenoxy (each optionally possessing 1 to 3 substituents selected from the group consisting of F, Cl, Br, CN, CF$_3$, NO$_2$, and CH$_3$), is a preferred embodiment of the invention.

A process for the preparation of N-arylarylsulfonamide compounds of Formula III wherein AR represents an aromatic moiety selected from
a) a substituted phenyl moiety of the formula:

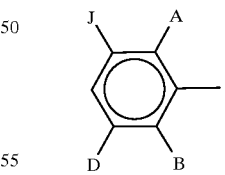

wherein
A represents F, Cl, Br, NO$_2$, CN, C$_1$–C$_4$ fluoroalkyl, CO$_2$(C$_1$–C$_4$ alkyl), CONH(C$_1$–C$_4$ alkyl), CON(C$_1$–C$_4$ alkyl)$_2$, SO$_2$(C$_1$–C$_4$ alkyl), or SO$_2$(C$_1$–C$_4$ fluoroalkyl);
B represents C$_1$–C$_4$ alkyl, F, Cl, Br, O(C$_1$–C$_4$ alkyl), O(C$_1$–C$_4$ fluoroalkyl), S(C$_1$–C$_4$ alkyl), S(C$_1$–C$_4$ fluoroalkyl), N(C$_1$–C$_4$ alkyl)$_2$; or phenyl, phenoxy, or phenylthio each optionally possessing 1 to 3 substituents selected from the group consisting of F, Cl, Br, CN, CF$_3$, NO$_2$, and CH$_3$; and D and J each independently represents H or $CH_3$ with the proviso that at least one of D and J represents H;

b) a substituted 3-pyridinyl moiety of the formula:

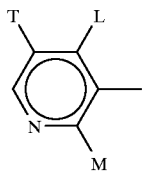

wherein

L and M each independently represents H, $C_1$–$C_4$ alkyl, $C_1$–$C_4$ fluoroalkyl, $O(C_1$–$C_4$ alkyl), $O(C_1$–$C_4$ fluoroalkyl), $O(C_2$–$C_4$ alkoxyalkyl), $O(C_3$–$C_4$ alkenyl), $O(C_3$–$C_4$ alkynyl), $S(C_1$–$C_4$ alkyl), $S(C_1$–$C_4$ fluoroalkyl), $SO_2(C_1$–$C_4$ alkyl), $SO_2(C_1$–$C_4$ fluoroalkyl), F, Cl, Br, I, CN, $NO_2$, $C_6H_5$, $CO_2(C_1$–$C_4$ alkyl), $CO_2(C_3$–$C_4$ alkenyl), $CO_2(C_3$–$C_4$ alkynyl), $CON(C_1$–$C_4$ alkyl)$_2$, or $CONH(C_1$–$C_4$ alkyl), with the proviso that not more than one of L and M represents H; and T represents H, F, Cl, Br, I, $CH_3$, or $CF_3$; or c) a 3-, 4-, or 5-pyrazolyl moiety substituted with a $C_1$–$C_3$ alkyl group in the 1-position, with at least one Cl, Br, I, or $CF_3$ and, optionally, with one $OCH_3$ or $CH_3$ group are sometimes especially preferred. Such compounds wherein Q represents 5-amino-1,2,4-triazin-3-yl or a [1,2,4]triazolo[1,5-a]pyrimidin-2-yl, [1,2,4]triazolo-[1,5-c]pyrimidin-2-yl, or [1,2,4]triazolo[1,5-a]pyridin-2-yl moiety each substituted with one or more F, Cl, Br, I, $C_1$–$C_3$ alkyl, $C_1$–$C_3$ fluoroalkyl, $O(C_1$–$C_3$ alkyl) groups constitute a class of special interest because the resulting compounds of Formula III are valuable herbicidal compounds or are intermediates for the preparation of valuable herbicidal compounds.

The invention further includes substituted N-arylsulfilimine compounds of Formula I:

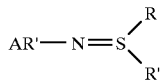

wherein

R represents methyl, ethyl, or n-propyl;

R' represents R, benzyl, or phenyl;

or R and R' together represent tetramethylene; and

AR' represents an aromatic moiety selected from a) a substituted phenyl moiety of the formula:

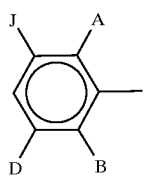

wherein

A represents F, Cl, Br, $NO_2$, CN, $C_1$–$C_4$ fluoroalkyl, $CO_2(C_1$–$C_4$ alkyl), $CONH(C_1$–$C_4$ alkyl), $CON(C_1$–$C_4$ alkyl)$_2$, $SO_2(C_1$–$C_4$ alkyl), or $SO_2(C_1$–$C_4$ fluoroalkyl);

B represents $C_1$–$C_4$ alkyl, F, Cl, Br, $O(C_1$–$C_4$ alkyl), $O(C_1$–$C_4$ fluoroalkyl), $S(C_1$–$C_4$ alkyl), $S(C_1$–$C_4$ fluoroalkyl), $N(C_1$–$C_4$ alkyl)$_2$; or phenyl, phenoxy, or phenylthio each optionally possessing 1 to 3 substituents selected from the group consisting of F, Cl, Br, CN, $CF_3$, $NO_2$, and $CH_3$; and D and J each independently represents H or $CH_3$ with the proviso that at least one of D and J represents H;

b) a substituted 3-pyridinyl moiety of the formula:

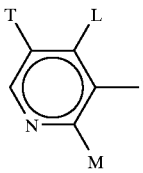

wherein

L and M each independently represents H, $C_1$–$C_4$ alkyl, $C_1$–$C_4$ fluoroalkyl, $O(C_1$–$C_4$ alkyl), $O(C_1$–$C_4$ fluoroalkyl), $O(C_2$–$C_4$ alkoxyalkyl), $O(C_3$–$C_4$ alkenyl), $O(C_3$–$C_4$ alkynyl), $S(C_1$–$C_4$ alkyl), $S(C_1$–$C_4$ fluoroalkyl), $SO_2(C_1$–$C_4$ alkyl), $SO_2(C_1$–$C_4$ fluoroalkyl), F, Cl, Br, I, CN, $NO_2$, $C_6H_5$, $CO_2(C_1$–$C_4$ alkyl), $CO_2(C_3$–$C_4$ alkenyl), $CO_2(C_3$–$C_4$ alkynyl), $CON(C_1$–$C_4$ alkyl)$_2$, or $CONH(C_1$–$C_4$ alkyl), with the proviso that not more than one of L and M represents H; and T represents H, F, Cl, Br, I, $CH_3$, or $CF_3$; or c) a 3-, 4-, or 5-pyrazolyl moiety substituted with a $C_1$–$C_3$ alkyl group in the 1-position, with at least one Cl, Br, I, or $CF_3$ and, optionally, with one $OCH_3$ or $CH_3$ group.

DETAILED DESCRIPTION OF THE INVENTION

The catalytic N-arylsulfilimine compounds of the invention, which can be represented by Formula I:

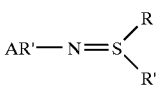

or, alternatively, by Formula Ia:

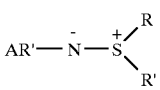

are characterized by having a semipolar nitrogen-sulfur bond. This bond can be depicted as a double bond, the sulfur atom of which is tetravalent as in Formula I, or can be depicted as single bond, the nitrogen atom of which is negatively charged and the sulfur atom of which is positively charged as in Formula Ia. Compounds possessing such bonds are often referred to as ylides. For simplicity, the sulfilimine compounds of the invention are depicted herein as being compounds having the structure of Formula I with the understanding that these compounds are the same as compounds depicted as having the structure of Formula Ia.

The substituents on the sulfur atom are R and R' wherein R represents methyl, ethyl, or n-propyl and R' represents R, phenyl, or benzyl; or wherein R and R' together represent tetramethylene. Such compounds wherein R and R' both represents methyl are generally preferred. The moiety attached to the nitrogen atom is AR which represents an aromatic hydrocarbyl or aromatic heterocyclyl moiety. This definition is inclusive of all aromatic hydrocarbyl and aromatic heterocyclyl moieties whether or not these moieties possess substituents. Examples of suitable aromatic hydrocarbyl moieties include phenyl, naphthyl, phenanthrenyl, and indenyl. Examples of suitable aromatic heterocyclyl moieties include pyridinyl, pyrimidinyl, pyridazinyl, pyrazinyl, 1,3,5-triazinyl, quinolinyl, quinazolinyl, quinoxalinyl, furanyl, thienyl, pyrrolyl, oxazolyl, thiazolyl, imidazolyl, pyrazolyl, 1,3,4-oxadiazolyl, 1,2,4-oxadiazolyl, 1,3,4-thiadiazolyl, 1,2,4-thiadiazolyl, 1,2,4-triazolyl, benzofuranyl, benzo[b]thienyl, indolyl, [1,2,4]triazolo[1,5-a]pyrimidinyl, [1,2,4]triazolo-[1,5-c]pyrimidinyl, [1,2,4]triazolo[1,5-a]pyridinyl, pyrazolo[1,5-a]pyrimidinyl, and [1,2,4]triazolo[1,5-a]-[1,3,5]triazinyl. AR' is preferably a substituted phenyl moiety, a substituted pyridinyl moiety, or a substituted pyrazolyl moiety. Compounds wherein AR' represents a substituted phenyl or substituted pyridinyl moiety are often of special interest.

The substituents possessed by the aromatic hydrocarbyl and heterocyclyl moieties AR' include any substituent that is stable in the presence of the other substituents in the N-arylsulfilimine compound and which does not react with the starting materials used to make the sulfilimine compound. Suitable substituents include F, Cl, Br, I, $NO_2$, CN, $C_1$–$C_8$ alkyl, $O(C_1$–$C_8$ alkyl), $O(C_3$–$C_8$ alkenyl), $O(C_3$–$C_8$ alkenyl), $N(C_1$–$C_8$ alkyl)$_2$, $S(C_1$–$C_8$ alkyl), $S(C_3$–$C_8$ alkenyl), $S(C_3$–$C_8$ alkenyl), $SO_2(C_1$–$C_8$ alkyl), $SO_2(C_3$–$C_8$ alkenyl), $SO_2(C_3$–$C_8$ alkenyl), $CO_2(C_1$–$C_8$ alkyl), $CO_2(C_3$–$C_8$ alkenyl), $CO_2(C_3$–$C_8$ alkenyl), $CONH(C_1$–$C_8$ alkyl), $CON(C_1$–$C_8$ alkyl)$_2$, $Si(C_1$–$C_8$ alkyl)$_3$, phenyl, phenoxy, thiophenoxy, pyridinyloxy, and pyridinylthio. Each alkyl in the substituents noted above can be mono to completely substituted with fluorine or mono or disubstituted with, for example, Cl, Br, I, $NO_2$, CN, $C_1$–$C_8$ alkyl, $O(C_1$–$C_8$ alkyl), $N(C_1$–$C_8$ alkyl)$_2$, $S(C_1$–$C_8$ alkyl), or $SO_2$ ($C_1$–$C_8$ alkyl), $CO_2(C_1$–$C_8$ alkyl), $CONH(C_1$–$C_8$ alkyl), $CON(C_1$–$C_8$ alkyl)$_2$, or $Si(C_1$–$C_8$ alkyl)$_3$. Each phenyl, phenoxy, thiophenoxy, pyridinyloxy, and pyridinylthio moiety in the substituents noted above can be mono to trisubstituted with, for example, F, Cl, Br, I, $NO_2$, CN, $C_1$–$C_8$ alkyl, $O(C_1$–$C_8$ alkyl), $N(C_1$–$C_8$ alkyl)$_2$, $S(C_1$–$C_8$ alkyl), or $SO_2(C_1$–$C_8$ alkyl), $CO_2(C_1$–$C_8$ alkyl), $CONH(C_1$–$C_8$ alkyl), $CON(C_1$–$C_8$ alkyl)$_2$, and $Si(C_1$–$C_8$ alkyl)$_3$.

Preferred substituents include F, Cl, Br, I, $NO_2$, CN, $O(C_3$–$C_4$ alkenyl), or $O(C_3$–$C_4$ alkynyl); $C_1$–$C_4$ alkyl, $O(C_1$–$C_4$ alkyl), $N(C_1$–$C_4$ alkyl)$_2$, $S(C_1$–$C_4$ alkyl), $SO_2$ ($C_1$–$C_4$ alkyl), $CO_2(C_1$–$C_4$ alkyl), $CONH(C_1$–$C_4$ alkyl), or $CON(C_1$–$C_4$ alkyl)$_2$ (each alkyl optionally mono to completely substituted with fluorine); or phenyl or phenoxy (each optionally possessing 1 to 3 substituents selected from the group consisting of F, Cl, Br, CN, $CF_3$, $NO_2$, and $CH_3$). Phenyl, pyridinyl, and 1-alkylpyrazolyl moieties possessing one to three such substituents are often preferred.

An embodiment of the invention that is often of special interest is compounds of Formula I wherein AR' represents a substituted phenyl moiety of the formula:

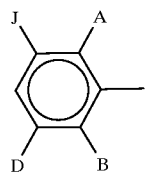

wherein A represents F, Cl, Br, $NO_2$, CN, $C_1$–$C_4$ fluoroalkyl, $CO_2(C_1$–$C_4$ alkyl), $CONH(C_1$–$C_4$ alkyl), $CON(C_1$–$C_4$ alkyl)$_2$, $SO_2(C_1$–$C_4$ alkyl), or $SO_2(C_1$–$C_4$ fluoroalkyl); B represents $C_1$–$C_4$ alkyl, F, Cl, Br, $O(C_1$–$C_4$ alkyl), $O(C_1$–$C_4$ fluoroalkyl), $S(C_1$–$C_4$ alkyl), $S(C_1$–$C_4$ fluoroalkyl), $N(C_1$–$C_4$ alkyl)$_2$, or phenyl, phenoxy, or phenylthio each optionally possessing 1 to 3 substituents selected from the group consisting of F, Cl, Br, CN, $CF_3$, $NO_2$, and $CH_3$; and D and J each independently represents H or $CH_3$ with the proviso that at least one of D and J represents H. Compounds of this type wherein A represents F, Cl, Br, $CF_3$, $NO_2$, or $CO_2CH_3$; B represents F, Cl, Br, $CH_3$, $OCH_3$; D represents H or $CH_3$; and J represents H are often preferred. Such compounds wherein AR' represents 2,6-dichlorophenyl, 2,6-difluorophenyl, 2-chloro-6-fluorophenyl, 2-methoxycarbonyl-6-methylphenyl, 2-chloro-6-methoxycarbonylphenyl, 2-fluoro-6-methoxycarbonylphenyl, 2-methoxy-6-(trifluoromethyl) phenyl, 2,6-dichloro-3-methylphenyl, and 2,6-difluoro-3-methylphenyl are often especially preferred.

Another embodiment of the invention that is often of special interest is compounds of Formula I wherein AR' represents a substituted 3-pyridinyl moiety of the formula:

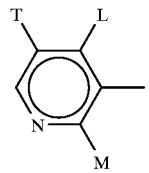

wherein L and M each independently represents H, $C_1$–$C_4$ alkyl, $C_1$–$C_4$ fluoroalkyl, $O(C_1$–$C_4$ alkyl), $O(C_1$–$C_4$ fluoroalkyl), $O(C_2$–$C_4$ alkoxyalkyl), $O(C_3$–$C_4$ alkenyl), $O(C_3$–$C_4$ alkynyl), $S(C_1$–$C_4$ alkyl), $S(C_1$–$C_4$ fluoroalkyl), $SO_2(C_1$–$C_4$ alkyl), $SO_2(C_1$–$C_4$ fluoroalkyl), F, Cl, Br, I, CN, $NO_2$, $C_6H_5$, $CO_2(C_1$–$C_4$ alkyl), $CO_2(C_3$–$C_4$ alkenyl), $CO_2$ ($C_3$–$C_4$ alkynyl), $CONH(C_1$–$C_4$ alkyl)$_2$, or $CONH(C_1$–$C_4$ alkyl), with the proviso that not more than one of L and M represents H; and T represents H, F, Cl, Br, I, $CH_3$, or $CF_3$. Such compounds wherein AR' represents a 2-(chloro, bromo, or trifluoromethyl)-4-($C_1$–$C_3$ alkoxy or $C_3$–$C_4$ alkenoxy)-3-pyridinyl, 2-fluoro-4-($C_1$–$C_2$ alkyl)-3-pyridinyl, or 4-methoxycarbonyl-3-pyridinyl are often more preferred. Specifically preferred AR' moieties of this type include 2-fluoro-4-methyl-3-pyridinyl, 2-chloro-4-methoxy-3-pyridinyl, 2-chloro-4-ethoxy-3-pyridinyl, 2-chloro-4-(1-methylethoxy)-3-pyridinyl, 2-chloro-4-propoxy-3-pyridinyl, and 4-methoxycarbonyl-3-pyridinyl.

A third embodiment of the invention that is often of special interest is compounds of Formula I wherein AR' represents a 3-, 4-, or 5-pyrazolyl moiety substituted with a $C_1$–$C_3$ alkyl group in the 1-position, with at least one Cl, Br, I, or $CF_3$ and, optionally, with one $OCH_3$ or $CH_3$ group. Compounds of this type wherein AR' represents a 1-methyl-4-halo-3-pyrazolyl, 1-methyl-4 -halo-5-pyrazolyl, or 1-ethyl-3-(trifluoromethyl)-5-(methyl, methoxy, or halo)-4-pyrazolyl moiety are sometimes more preferred.

The term alkyl as employed herein includes linear, branched, and cyclic alkyl moieties. Examples include methyl, ethyl, 1-methylethyl, butyl, 2-methylpropyl, 1,1-dimethylethyl, cyclopropyl, and cyclopropylmethyl. The term fluoroalkyl includes alkyl moieties substituted with up to the maximum possible number of fluorine atoms. Examples include trifluoromethyl, 2-fluoroethyl, and 1,1,2,2-tetrafluoroethyl. The term halo includes fluoro, chloro, bromo, and iodo.

Some specifically preferred compounds of Formula I include S,S-dimethyl-N-(2,6-dichlorophenyl)sulfilimine, S,S-dimethyl-N-(2,6-dichloro-3-methylphenyl)sulfilimine, S,S-dimethyl-N-(2,6-difluorophenyl)sulfilimine, S,S-dimethyl-N-(2,6-difluoro-3-methylphenyl)sulfilimine, S,S-dimethyl-N-(2-chloro-6-fluorophenyl)sulfilimine, S,S-dimethyl-N-(2-methoxycarbonyl-6-chlorophenyl) sulfilimine, S,S-dimethyl-N-(2-methoxycarbonyl-6-fluorophenyl)sulfilimine, S,S-dimethyl-N-(2-methoxycarbonyl-6-methylphenyl)sulfilimine, S,S-dimethyl-N-(2-methoxy-6-(trifluoromethyl)phenyl) sulfilimine, S,S-dimethyl-N-(2-fluoro-4-methyl-3-pyridinyl)sulfilimine, S,S-dimethyl-N-(2-chloro-4-methoxy-3-pyridinyl)sulfilimine, S,S-dimethyl-N-(1-ethyl-5-methyl-3-(trifluoromethyl)-4-pyrazolyl)sulfilimine, S,S-dimethyl-N-(1-methyl-4-bromo-3-pyrazolyl)sulfilimine, and S,S-dimethyl-N-(1-methyl-4-bromo-5-pyrazolyl) sulfilimine.

The N-arylsulfilimine compounds of Formula I can be prepared by several general methods known in the art. The methods described in *Chemical Reviews,* 77, 409–435 (1977), *Synthesis,* 165–185 (1981), and *Russian Chemical Reviews,* 59, 819–831 (1990) and the references cited therein can be used with only routine adaptation.

It is often preferred to use the method of preparation involving the reaction of a sulfoxide compound of the formula:

wherein R and R' are as defined for compounds of Formula I with an arylamine compound of Formula IIIa:

wherein AR' is as defined for compounds of Formula I and an activator such as sulfur trioxide, 2-sulfobenzoic acid cyclic anhydride, trifluoroacetic anhydride, carbonyl chloride, or oxalyl chloride. The reaction mixture is treated with a base, such as an alkali metal hydroxide, to complete the process. The process is generally carried out at temperatures between about −70° C. and about 20° C. in an organic solvent, such as dichloromethane. Typically, a mixture of the activator and the solvent is prepared and cooled to the desired reaction temperature and the sulfoxide compound is then added. After a short reaction period, the arylamine compound is added and allowed to react for one to four hours. Finally, an aqueous solution of an alkali metal hydroxide is added and the phases are separated. The N-arylsulfilimine compound product can be recovered by evaporative removal of the volatile organic components of the reaction mixture and can be purified by conventional means, such as by recrystallization. It is not, however, necessary to recover the compound; the N-arylsulfilimine compound can be employed as a catalyst in the form of the solution in an organic solvent obtained on separation of the phases.

Alternately, the N-arylsulfilimine compounds of Formula I can be prepared by the reaction of a sulfide compound of the formula R—S—R' with an arylamine compound of Formula IIIa and chlorine. The process is generally carried out at temperatures between about −20° C. and about 20° C. in an organic solvent, such as dichloromethane. Typically, a solution of the sulfide compound in the solvent is prepared and cooled to the desired reaction temperature. Approximately one molar equivalent of chlorine is added and then approximately one molar equivalent each of the arylamine compound and an aromatic tertiary amine base, such as pyridine, a picoline, a collidine, a (mono or poly) halopyridine, nicotinamide, ethyl nicotinate, quinoline, and the like are added. Alternately, an aqueous base, such as an solution of an alkali metal hydroxide or carbonate can be employed as the base. After a short reaction period, a solution of an N-arylsulfilimine compound as a solution in an organic solvent is formed. The N-arylsulfilimine compound can be recovered by conventional means or can be used in the form of the solution in an organic solvent obtained. The aromatic tertiary amine hydrochloride by-product obtained when an aromatic tertiary amine base is used can be removed from the mixture by extraction with water before use, if desired.

The N-arylsulfilimine compounds of Formula I are useful as catalysts in the preparation of N-arylarylsulfonamide compounds of Formula IV:

by the reaction of aromatic sulfonyl chloride compounds of Formula II:

with arylamine compounds of Formula III:

wherein Q and AR each independently represents an aromatic hydrocarbyl or aromatic heterocyclyl moiety.

An N-arylsulfilimine compound of Formula I wherein the AR' moiety is identical with the AR moiety of the arylamine compound of Formula III is most often used and is highly preferable. The use of an N-arylsulfilimine catalyst wherein AR' is different from the AR moiety of the arylamine compound generally produces an N-arylarylsulfonamide compound of Formula IV wherein AR is the AR' of the N-arylsulfilimine catalyst in addition to the desired compound of Formula IV wherein AR is the AR moiety of the arylamine compound. This generally reduces the yield based on the sulfonyl chloride compound and can create a significant separation problem. It is essential that the AR' of the N-arylsulfilimine compound be identical with the AR of the arylamine compound when the N-arylarylsulfonamide compound prepared is an agricultural chemical or a pharmaceutical chemical because the commercial utility of such chemicals would be compromised by the presence of the related compounds that are formed when the AR' moiety is not identical with the AR moiety.

The AR moieties of the compounds of Formula III that are employed in the process of the invention are the same as those described and characterized herein for the AR' moieties of the N-arylsulfilimine catalysts of Formula I. The preferences for categories of AR, for substituents, and for specific substituent patterns are the same as those described for AR'.

The Q moiety of the compounds of Formula II represents an aromatic hydrocarbyl or aromatic heterocyclyl moiety. This definition is inclusive of all aromatic hydrocarbyl and aromatic heterocyclyl moieties whether or not these moieties possess substituents. Examples of suitable aromatic hydrocarbyl moieties include phenyl, naphthyl, phenanthrenyl, and indenyl. Examples of suitable aromatic heterocyclyl moieties include pyridinyl, pyrimidinyl, pyridazinyl, pyrazinyl, 1,3,5-triazinyl, quinolinyl, quinazolinyl, quinoxalinyl, furanyl, thienyl, pyrrolyl, oxazolyl, thiazolyl, imidazolyl, pyrazolyl, 1,3,4-oxadiazolyl, 1,2,4-oxadiazolyl, 1,3,4-thiadiazolyl, 1,2,4-thiadiazolyl, 1,2,4-triazolyl, benzofuranyl, benzo[b]thienyl, indolyl, [1,2,4]triazolo[1,5-a]pyrimidinyl, [1,2,4]triazolo-[1,5-c]pyrimidinyl, [1,2,4]triazolo[1,5-a]pyridinyl, pyrazolo[1,5-a]pyrimidinyl, and [1,2,4]triazolo[1,5-a]-[1,3,5]triazinyl. Sulfonyl chloride compounds wherein Q represents substituted phenyl are most often employed and processes involving such compounds, especially such compounds possessing one or two ortho-substituents, are therefore often preferred. Compounds wherein Q represents a substituted pyridinyl moiety, especially such compounds possessing at least one ortho-substituent are also sometimes preferred. Sulfonyl chloride compounds wherein Q represents 5-amino-1,2,4-triazin-3-yl or a substituted [1,2,4]triazolo[1,5-c]pyrimidine-2-yl, [1,2,4]triazolo[1,5-a]pyrimidine-2-yl, or [1,2,4]triazolo[1,5-a]pyridine-2-yl moiety are often of special interest.

The substituents possessed by the aromatic hydrocarbyl and heterocyclyl moieties Q include any substituent that is stable in the presence of the other substituents in the aryl sulfonyl chloride compound and which does not react with the arylamine compound or the sulfilimine catalyst. Suitable substituents include F, Cl, Br, I, $NO_2$, CN, $C_1$–$C_8$ alkyl, $O(C_1$–$C_8$ alkyl), $O(C_3$–$C_8$ alkenyl), $O(C_3$–$C_8$ alkenyl), $N(C_1$–$C_8$ alkyl)$_2$, $S(C_1$–$C_8$ alkyl), $S(C_3$–$C_8$ alkenyl), $S(C_3$–$C_8$ alkenyl), $SO_2(C_1$–$C_8$ alkyl), $SO_2(C_3$–$C_8$ alkenyl), $SO_2(C_3$–$C_8$ alkenyl), $CO_2(C_1$–$C_8$ alkyl), $CO_2(C_3$–$C_8$ alkenyl), $CO_2(C_3$–$C_8$ alkenyl), $CONH(C_1$–$C_8$ alkyl), $CON(C_1$–$C_8$ alkyl)$_2$, $Si(C_1$–$C_8$ alkyl)$_3$, phenyl, phenoxy, thiophenoxy, pyridinyloxy, and pyridinylthio. Each alkyl in the substituents noted above can be mono to completely substituted with fluorine or mono or disubstituted, for example, with Cl, Br, I, $NO_2$, CN, $C_1$–$C_8$ alkyl, $O(C_1$–$C_8$ alkyl), $N(C_1$–$C_8$ alkyl)$_2$, $S(C_1$–$C_8$ alkyl), or $SO_2(C_1$–$C_8$ alkyl), $CO_2(C_1$–$C_8$ alkyl), $CONH(C_1$–$C_8$ alkyl), $CON(C_1$–$C_8$ alkyl)$_2$, and $Si(C_1$–$C_8$ alkyl)$_3$. Each phenyl, phenoxy, thiophenoxy, pyridinyloxy, and pyridinylthio moiety in the substituents noted above can be mono to trisubstituted with, for example, F, Cl, Br, I, $NO_2$, CN, $C_1$–$C_8$ alkyl, $O(C_1$–$C_8$ alkyl), $N(C_1$–$C_8$ alkyl)$_2$, $S(C_1$–$C_8$ alkyl), or $SO_2(C_1$–$C_8$ alkyl), $CO_2(C_1$–$C_8$ alkyl), $CONH(C_1$–$C_8$ alkyl), $CON(C_1$–$C_8$ alkyl)$_2$, or $Si(C_1$–$C_8$ alkyl)$_3$.

Preferred substituents include F, Cl, Br, I, $NO_2$, CN, $O(C_3$–$C_4$ alkenyl), or $O(C_3$–$C_4$ alkynyl); $C_1$–$C_4$ alkyl, $O(C_1$–$C_4$ alkyl), $N(C_1$–$C_4$ alkyl)$_2$, $S(C_1$–$C_4$ alkyl), $SO_2(C_1$–$C_4$ alkyl), $CO_2(C_1$–$C_4$ alkyl), $CONH(C_1$–$C_4$ alkyl), or $CON(C_1$–$C_4$ alkyl)$_2$ (each alkyl optionally mono to completely substituted with fluorine); or phenyl or phenoxy (each optionally possessing 1 to 3 substituents selected from the group consisting of F, Cl, Br, CN, $CF_3$, $NO_2$, and $CH_3$).

Sulfonyl bromide or fluoride compounds corresponding to the sulfonyl chloride compounds of Formula II could be employed in the process of the invention in place of the compounds of Formula II. Sulfonyl bromide and fluoride compounds, however, are not generally commercially available, especially at a cost comparable to the cost of the compounds of Formula II, and are not commonly used.

Some specifically preferred sulfonyl chloride compounds of Formula II for use in the process of the invention include 2-chlorosulfonyl-5-ethoxy-7-fluoro[1,2,4]triazolo[1,5-c]pyrimidine, 2-chlorosulfonyl-5-methoxy-8-fluoro[1,2,4]triazolo[1,5-c]pyrimidine, 2-chlorosulfonyl-5-methoxy-7-methyl[1,2,4]triazolo[1,5-c]pyrimidine, 2-chlorosulfonyl-5-ethoxy-7-methyl[1,2,4]triazolo[1,5-c]pyrimidine, 2-chlorosulfonyl-5-methyl[1,2,4]triazolo[1,5-a]pyrimidine, 2-chlorosulfonyl-5,7-dimethoxy[1,2,4]triazolo[1,5-a]pyrimidine, 2-chlorosulfonyl-5,7-dimethyl[1,2,4]triazolo[1,5-a]pyrimidine, 2-chlorosulfonyl-5-methoxy-7-methyl[1,2,4]triazolo[1,5-a]pyridine, and 2-chlorosulfonyl-5-methoxy-8-chloro[1,2,4]triazolo[1,5-a]pyridine.

The process is carried out by contacting a sulfonyl chloride compound of Formula II with an arylamine compound of Formula III in the presence of an aromatic tertiary amine base compound and an added catalytic amount of an N-arylsulfilimine compound of Formula I:

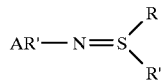

wherein AR', R, and R' are as defined hereinabove, preferably wherein AR is selected to be identical with AR in the arylamine compound. Any of the known procedures for contacting the reactants and catalyst can be used. For example, the sulfonyl chloride compound of Formula II can be mixed with an organic solvent and then an arylamine compound of Formula III, a molar equivalent or more of an aromatic tertiary amine base, such as pyridine, a picoline, a collidine, a (mono or poly)halopyridine, nicotinamide, quinoline, and the like, and a catalytically effective amount of an N-arylsulfilimine compound of Formula I are added. The amount of arylamine compound of Formula III employed—including the arylamine compound contained in the N-arylsulfilimine catalyst—is at least about one molar equivalent. Amounts in excess of one molar equivalent are not deleterious to the process, but are generally not necessary. The reagents can be combined in any order. It is frequently preferred to prepare the N-arylsulfilimine catalyst of Formula I in a vessel and add the arylamine compound of Formula III, the sulfonyl chloride compound of Formula II, and the aromatic tertiary amine base to it. When AR of the arylamine reactant and AR' of the sulfilimine catalyst are selected to be identical, the arylamine reactant of Formula III can be present during the preparation of the N-arylsulfilimine catalyst; that is, an excess of arylamine can be used in the preparation of the N-arylsulfilimine catalyst and the excess employed as all or a portion of the arylamine reactant in the process. The desired N-arylarylsulfonamide product of Formula IV is prepared in the resulting reaction.

A catalytically effective amount of the N-arylsulfilimine compounds of Formula I can be determined readily for each N-arylarylsulfonamide preparation by routine experimentation. In most instances an amount between about 2 and about 30 mole percent of the amount of sulfonyl chloride compound of Formula II is employed.

The process is generally carried out at a temperature of between about −20° C. and about 50° C. The lower limit is because the reaction becomes too slow to be practical at very low temperatures and the higher limit is because the N-arylsulfilimine catalysts become unstable at elevated temperatures. Temperatures of between about 0° C. and about 30° C. are often preferred. The pressure in the reactor is not believed to be critical; pressures close to atmospheric are generally preferred. Continuous and effective mixing is usually helpful. A reaction period of 30 minutes to about 16 hours is typical for the process to go to completion. The reaction is generally carried out under essentially anhydrous conditions.

Solvents that are suitable for such processes are organic solvents in which the aromatic sulfonyl chloride compound of Formula II, the N-arylsulfilimine compound of Formula I, and the arylamine compound of Formula III have at least some solubility and which are inert with respect to the reagents employed. Suitable solvents include acetonitrile, butyronitrile, benzonitrile, dichloromethane, 1,2-dichloroethane, tetrahydrofuran, 1,2-dimethoxyethane, toluene, chlorobenzene, and the like. Sufficient organic solvent is employed to facilitate stirring of the reaction mixture and, thereby, to achieve homogeneity and promote good contact between the reagents.

The aromatic tertiary amine base employed is a factor in determining the results obtained. Pyridine or a picoline (2-, 3-, or 4-picoline, or a mixture) are often preferred because they are the least expensive. Quinoline and nicotinamide are also sometimes preferred because, in some instance, higher yields are realized. The base that is optimum in any specific situation depends on the nature of the other reagents employed, including the N-arylsulfilimine catalyst, and the nature (particularly the pKa) of the N-arylarylsulfonamide product being prepared. The formation of by-product N-arylbisarylsulfonimide can be minimized and the yield of the desired N-arylarylsulfonamide can be maximized by the selection of the most appropriate tertiary amine base. The optimum aromatic tertiary amine base for any combination of aryl sulfonyl chloride compound and arylamine compound can be determined by routine experimentation.

The N-arylarylsulfonamide products of Formula IV can be recovered from the process medium by standard procedures, including by filtration to collect insoluble solids and by extracting the final reaction mixture with water and removing the solvent and any other volatile materials by evaporation, preferably under reduced pressure. The products obtained on recovery can generally be purified standard procedures, such as by recrystallization.

The aromatic sulfonyl chloride compounds of Formula II and the arylamine compounds of Formula III are known in the art or can be prepared by routine adaptation of the methods disclosed in the art.

The following examples are provided to illustrate the invention. They should not be construed as limiting the claims.

EXAMPLES

1. Preparation of N-(2,6-Difluorophenyl)-S,S-dimethylsulfilimine

A slurry of 2.39 g (grams) (13.0 mmol (millimoles)) of 2-sulfobenzoic acid cyclic anhydride in 20 mL (milliliters) of dichloromethane was prepared and cooled to 3° C. To this 0.85 mL (0.94 g, 12 mmol) of dimethyl sulfoxide (DMSO) was added dropwise over a 1-min period with stirring and cooling. The temperature rose to 5° C. and the mixture became homogeneous. After 5 min, 1.41 g (11 mmol) of 2,6-difluoroaniline was added with stirring and cooling over a 2-min period. A white precipitate formed and the temperature rose to 9° C. After 2 hours the precipitate, which amounted to 3.2 g, was collected by filtration and slurried in 15 mL of fresh dichloromethane. Ten mL of 2N aqueous sodium hydroxide was added and the mixture was agitated. The two clear liquid phases that formed were separated and the organic phase was dried over magnesium sulfate and concentrated by evaporation under reduced pressure to obtain a clear oil. This oil was dissolved in 5 mL of ether and 5 mL of cyclohexane was added. The mixture was cooled to 5° C. and the white needles that formed were collected by filtration and dried to obtain 0.88 g of the title compound.
$^1$H NMR [300 MHz] (CD$_3$CN) ppm: 6.80–6.75(m, 2H), 6.64–6.5(m, 1H), 2.70 (s, 6H); Mass Spectrum EI(m/z): 189(M$^+$, 75), 174(M$^+$-CH$_3$, 100), 159(M$^+$-C$_2$H$_6$, 90).

2. Preparation of N-(2,6-Dichlorophenyl)-S,S-dimethylsulfilimine

A slurry of 23.9 g (130 mmol) of 2-sulfobenzoic acid cyclic anhydride in 205 mL of dichloromethane was prepared and cooled to 4° C. To this 9.46 g, (120 mmol) of dimethyl sulfoxide was added in three portions over a 3- to 4-min period with stirring and cooling, rinsing the container with about 10 mL dichloromethane to ensure complete transfer. The temperature rose to between 5 and 6° C. After 10 min, 17.9 g (110 mmol) of 2,6-dichloroaniline was added with stirring and cooling over a 4-min period. A white precipitate formed. After 90 min the mixture was a thick slurry and the temperature was 15° C. The mixture was treated with 207 g of 1N and then 5 mL of 50 percent aqueous sodium hydroxide. The two clear liquid phases that formed were separated and the aqueous phase was extracted with 150 mL of dichloromethane. The organic phase and extract were combined and washed with 100 mL of water, dried over magnesium sulfate, filtered, and concentrated by evaporation under reduced pressure to obtain a light gold oil. This oil was crystallized from diethyl ether to obtain the title compound in two crops weighing 1.94 and 2.03 g (16 percent of theory) as a white solid.
$^1$H NMR [300 MHz] (CDCl$_3$) ppm: 7.21–7.18(d, 2H), 6.68–6.63 (dd, 1H), 2.68(s, 6H); Mass Spectrum EI(m/z): 221(M$^+$, 50), 206(M$^+$-CH$_3$, 100), 191(MH$^+$-C$_2$H$_6$, 45).

3. Preparation of N-(2-Chloro-6-methoxycarbonylphenyl)-S,S-dimethylsulfilimine Method A A solution of 5.0 mL (0.068 mol) of dimethyl sulfide in 80 mL of dichloromethane was prepared in a round bottom flask and cooled to −10° C. Gaseous chlorine (4.6 g, 0.065 mol) was added to the vapor space of the flask through a sparge tube with cooling and stirring and, after about 2 min, 12 g (0.065 mol) of methyl 3-chloroanthranilate (2-chloro-6-methoxycarbonylphenylamine) was added with stirring and cooling. After about 2 min, 10.2 g (0.13 mol) of pyridine was added slowly with stirring and cooling and the mixture was allowed to react at −10° C. for 10 min. The mixture was analyzed by HPLC (high pressure liquid chromatography) (Shandon Hypersil Phenyl 5 mm packing, 60:40:01 acetonitrile:water:phosphoric acid eluent, and uv detector set at 237 nm (nanometers)) and found to be 20 percent methyl 3-chloroanthranilate and 80 percent the title compound (normalized over these two substances). The volatile components of the mixture were removed by evaporation under reduced pressure to obtain the title compound in crude form as a white solid.
$^1$H NMR [300 MHz] (CDCl$_3$) ppm: 7.82(dd, 1H, J=1.3, 8.1), 7.69(dd, 1H, J=1.3, 8.1), 7.33(t, 1H, J=8.1), 3.89(s, 3H), 3.37(s, 6H); Ultraviolet Spectrum: maxima at 213 and 298 nm; Mass Spectrum EI(m/z): 246(MH$^+$, 60), 184(M$^+$-SC$_2$H$_6$, 100), 154(M$^+$-OSC$_3$H$_8$, 65).

The following compounds were prepared similarly:
N-(2-chlorophenyl)-S,S-dimethylsulfilimine
$^1$H NMR [300 MHz] (CD$_3$CN) ppm: 7.52(dd, 1H, J=7.7, 1.7), 7.49(dd, 1H, J=7.7, 1.8), 7.35(dt, 1H, J=7.6, 1.7), 7.29(dt, 1H, J=7.6, 1.7), 2.56(s, 6H); Ultraviolet Spectrum: maxima at 210 and 260 nm;
N-(2-methoxy-6-(trifluoromethyl)phenyl)-S,S-dimethylsulfilimine
$^1$H NMR [300 MHz] (CD$_3$CN) ppm: 7.43(t, 1H, J=8.0), 7.30(d, 1H, J=8.0), 7.24(d, 1H, J=8.0), 3.93(s, 3H), 3.29(s, 6H);
2,6-dichloro-3-methylphenyl)-S,S-dimethylsulfilimine
$^1$H NMR [300 MHz] (CD$_3$CN) ppm: 7.10(d, 1H, J=8.2), 6.61(d, 1H, J=8.2), 2.84(s, 6H), 2.27(s, 3H); Mass spectrum EI(m/z): 236(MH$^+$), 208, 195, 174, 147;

N-(2-methoxycarbonylphenyl)-S,S-dimethylsulfilimine $^1$H NMR [300 MHz] (CD$_3$CN) ppm: 7.92(dd, 1H, J=8.0, 1.5), 7.48(dt, 1H, J=7.8, 1.4), 7.14(d, 1H, J=8.1), 7.06(dt, 1H, J=8.1, 1.0), 3.85(s, 3H), 2.56(s, 6H);

N-(2-methyl-6-nitrophenyl)-S,S-dimethylsulfilimine $^1$H NMR [300 MHz] (CD$_3$CN) ppm: 7.82(d, 1H, J=8.2), 7.58(d, 1H, J=7.4), 7.34(brdd, 1H, J=7.8, 7.3), 3.38(s, 6H), 2.48(s, 3H); $^{13}$C NMR [75.5 MHz] (CD$_3$CN) ppm: 146.0, 138.5, 137.4, 132.6, 128.2, 124.6, 33.9, 19.3;

N-(2-chloro-4-(1-methylethoxy)-3-pyridinyl)-S,S-dimethylsulfilimine $^1$H NMR [300 MHz] (CD$_3$CN) ppm: 8.08(d, 1H, J=5.8), 7.03(d, 1H, J=5.8), 4.8(septet, 1H, J=6.1), 3.26(s, 6H), 1.37(d, J=6.0, 6H);

N-(5-bromo-2-pyridinyl)-S,S-dimethylsulfilimine $^1$H NMR [300 MHz] (CD$_3$CN) ppm: 8.21(d, 1H, J=2.3), 7.74(dd, 1H, J=8.8, 2.4), 6.98(d, 1H, J=8.8), 3.36(s, 6H).

Method B

A mixture of 7.3 g (94 mmol) of dimethyl sulfoxide and 100 mL of dichloromethane was prepared and cooled to −60° C. and then 19.8 g (94 mmol) of trifluoroacetic anhydride was added slowly with stirring. A white solid formed in about 5 min at which time a solution of 24 g (130 mmol) of methyl 6-chloroanthranilate in 15 mL of dichloromethane was added slowly with stirring. The mixture was allowed to react and warm to about 0° C. with stirring. The white solid that first formed redissolved. The mixture was then neutralized with 70 mL of 10 weight percent potassium hydroxide in water with stirring for 30 min. The mixture turned brown. The organic phase was separated and the aqueous phase was extracted twice with dichloromethane. The organic phase and the extracts were combined and concentrated by evaporation under reduced pressure. The brown tarry residue was triturated with diethyl ether to induce solidification, recovered by filtration, and washed with diethyl ether to obtain the title compound in crude form as a greenish brown solid. The solid was found by HPLC to consist of about 80 percent the title compound and about 20 percent methyl 6-chloroanthranilate.

Method C

A solution of 3.2 g (0.039 mol) of sulfur trioxide in 6 mL of dichloromethane was cooled to 0° C. and 1.4 g (0.018 mol) of dimethyl sulfoxide was slowly added with stirring and cooling. After 10 min, 3.3 g (0.018 mol) of methyl 6-chloroanthranilate was added as a solid with stirring and cooling. The mixture was allowed to react for 15 min and then 2.8 g (0.035 mol) of pyridine was added. The resulting solution was determined by HPLC to contain the title compound and unreacted methyl 6-chloroanthranilate in a 61:39 ratio.

4. Preparation of N-(2-Chloro-6-methoxycarbonylphenyl)-S,S-tetramethylenesulfilimine A solution of 3.0 mL (34 mmol) of tetrahydrothiophene and 50 mL of dichloromethane was cooled to −10° C. and then 2.3 g (32 mmol) of chlorine was sparged in with cooling and stirring. A 6.3 g (34 mmol) amount of methyl 6-chloroanthranilate and then 5.4 g (68 mmol) of pyridine were added. The ratio of the title compound to unreacted methyl 6-chloroanthranilate in the product mixture was found to be 65:35 by HPLC.

$^1$H NMR [300 MHz] (CD$_3$CN) ppm: 7.78(d, 1H, J=8.0), 7.44(d, 1H, J=8.0), 6.64(t, 1H, J=8.0), 3.63(s, 3H), 3.24(m, 4H), 2.37(m, 2H), 2.16(m, 2H); Ultraviolet Spectrum: maximum at 220 nm; Mass Spectrum EI(m/z): 272(MH$^+$, 100), 240(M$^+$-OCH$_4$, 15), 184(M$^+$-SC$_4$H$_8$, 100), 87(SC$_4$H$_7^+$, 40).

5. Preparation of N-(2-Chloro-6-methoxycarbonylphenyl)-S-methyl-S-phenylsulfilimine A solution of 3.0 g (24 mmol) of methyl phenyl sulfide in 30 mL of dichloromethane was cooled to −10° C. and 1.7 g (24 mmol) of chlorine was sparged in with cooling and stirring. To this was added with cooling and stirring 4.5 g (24 mmol) of solid methyl 6-chloroanthranilate and then 3.8 g (48 mmol) of pyridine. The product mixture contained the title compound and methyl 6-chloroanthranilate in a 60:40 ratio as determined by HPLC.

Ultraviolet Spectrum: maxima at 215 and 300 nm; Mass Spectrum EI(m/z): 308(MH$^+$, 40), 276(M$^+$-OCH$_4$, 35), 261 (M$^+$-OC$_2$H$_7$, 10), 184(M$^+$-SC$_7$H$_8$, 35), 124(SC$_7$H$_8^+$, 40).

6. Preparation of N-(2,4,6-Trichlorophenyl)-S,S-dimethylsulfilimine

A solution of 1.1 mL (15 mmol) of dimethyl sulfide in 170 mL of dichloromethane was cooled to −10° C. and 0.90 g (13 mmol) of chlorine was added through a sparge tube with cooling and stirring. Subsequently, 23.3 g (120 mmol) of 2,4,6-trichloroaniline and then 22 g (170 mmol) of quinoline were added with cooling and stirring. The resulting product was a mixture of the title compound and unreacted 2,4,6-trichloroaniline.

7. Preparation of N-(4-Bromo-1-methyl-5-pyrazolyl)-S,S-dimethylsulfilimine

A solution of 0.60 mL (8.2 mmol) of dimethyl sulfide in 30 mL of dichloromethane was cooled to −20° C. and 0.50 g (7.0 mmol) of chlorine was added through a sparge tube with cooling and stirring. Subsequently, 1.0 g (5.7 mmol) of 5-amino-4-bromo-1-methylpyrazole and then 1.0 g (12.7 mmol) of pyridine were added with cooling and stirring. A 2 mL aliquot of this mixture was removed and the light yellow solids present were collected by filtration and washed with deuteroacetonitrile.

$^1$H NMR [300 MHz] (CD$_3$CN/D$_2$O) ppm: 7.58(s, 1H), 3.77(s, 3H), 3.17(s, 6H).

8. Preparation of N-(2,6-Difluorophenyl)-8-fluoro-5-methoxy[1,2,4]triazolo[1,5-c]pyrimidine-2-sulfonamide Using Sulfilimine Catalyst A mixture consisting of 1.4 g (11 mmol) of 2,6-difluoroaniline, 0.86 g (11 mmol) of pyridine, and 30 mL of dry acetonitrile was prepared and cooled to 1–3° C. N-(2, 6-difluorophenyl)-S,S-dimethylsulfilimine (0.15 g, 0.78 mmol) was added and then 2.7 g (10 mmol) of 2-chlorosulfonyl-8-fluoro-5-methoxy[1,2,4]triazolo[1,5-c] pyrimidine in 10 mL of dry acetonitrile was added dropwise over a 30-sec period with stirring and cooling to the yellow solution. An exotherm raising the temperature to 10° C. was observed and a white precipitate gradually formed. After 80 min, the mixture was quantitatively analyzed by HPLC using standards and it was found that of the chlorosulfonyl compound 70 percent was converted to the title compound, 24 percent was converted to N,N-bis((8-fluoro-5-methoxy [1,2,4]triazolo[1,5-c]pyrimidin-2-yl)sulfonyl)-2,6-difluorophenylamine and 4 percent was converted to 8-fluoro-5-methoxy[1,2,4]triazolo[1,5-c]pyrimidine-2-sulfonic acid.

9. Preparation of N-(2,6-Dichlorophenyl)-7-fluoro-5-ethoxy[1,2,4]triazolo [1,5-c]-pyrimidine-2-sulfonamide Using Sulfilimine Catalyst A mixture consisting of 7.33 g (42.5 mmol) of 2,6-dichloroaniline, 14.13 g (47.4 mmol) of 94.2 percent purity 2-chlorosulfonyl-7-fluoro-5-ethoxy[1,2,4]triazolo[1,5-c]pyrimidine, 6.72 g (55.0 mmol) of nicotinamide, and 81.4 g of dry acetonitrile was prepared and cooled to 4° C. N-(2,6-Dichlorophenyl)-S,S-dimethylsulfilimine (1.15 g, 5.15 mmol) was then added with stirring and cooling. Cooling and stirring were maintained for 3 hours and then the mixture was allowed to warm to ambient temperature. After 6 hours, the mixture was quantitatively analyzed by HPLC using standards and the yield of the title compound was found to be 87 percent of theory. A 3 percent yield of 7-fluoro-5-ethoxy[1,2,4]triazolo[1,5-c]pyrimidine-2-sulfonic acid was also found.

10. Preparation of N-(2-Chloro-6-methoxycarbonylphenyl)-7-fluoro-5-ethoxy[1,2,4]triazolo[1,5-c]pyrimidine-2-sulfonamide Using Unrecovered Sulfilimine Catalyst A solution of 0.7 mL (96 mmol) of dimethyl sulfide in 20 mL of dichloromethane was prepared in a round bottom flask and cooled to −10° C. Gaseous chlorine (0.60 g, 85 mmol) was added to the vapor space of the flask through a sparge tube with cooling and stirring and, after about 2 min, 18 g (97 mmol) of methyl 3-chloroanthranilate (2-chloro-6-methoxycarbonylphenylamine) was added with stirring and cooling. After about 2 min, 9.8 g (124 mmol) of pyridine was added slowly with stirring and cooling and the mixture was allowed to react at −10° C. for 10 min. A solution of 21 g (75 mmol) of 2-chlorosulfonyl-7-fluoro-5-ethoxy[1,2,4]triazolo[1,5-c]pyrimidine in 90 mL of dichloromethane was prepared, cooled to 0° C., and then added with cooling and stirring. The reaction was essentially complete by HPLC analysis in 5–6 hours. After standing overnight, about 50 mL of the dichloromethane was removed by distillation and 50 mL of 2-propanol was added. The remaining dichloromethane was removed by distillation until the overhead temperature was 62–64° C. and the pot temperature was 72–74° C. The resulting 2-propanol slurry was cooled to 5° C. and, after 30 min, was filtered. The solids collected were rinsed with 2×50 mL of methanol and air dried to obtain 29.8 g (85 percent of theory) of the title compound.

The same product was obtained in a similar fashion using the N-(2-chloro-6-methoxycarbonylphenyl)-S,S-tetramethylenesulfilimine product mixture of Example 4 as the catalyst. A 9 mL portion of that product was diluted with 75 mL of dichloromethane, the solution was cooled to 10° C., and 9.3 g (50 mmol) of methyl 3-chloroanthranilate and then 4.8 g (60 mmol) of pyridine were added with cooling and stirring. 2-Chlorosulfonyl-7-fluoro-5-ethoxy[1,2,4]triazolo[1,5-c]pyrimidine (15.5 g of 91 percent pure, 50 mmol) was added with cooling to 0–2° C. The reaction was complete in 6 hours and a 90 percent yield of 98 percent purity title compound was obtained on recovery.

The same product was obtained in a similar fashion using the N-(2-chloro-6-methoxycarbonylphenyl)-S-methyl-S-phenylsulfilimine product mixture of Example 5 as the catalyst. A 55 percent yield of 98 percent purity product was obtained.

The following compounds were prepared in a similar manner using N-(2-chloro-6-methoxycarbonylphenyl)-S,S-dimethylsulfilimine as the catalyst:
N-(2-chloro-6-methoxycarbonylphenyl)-7,8-dichloro[1,2,4]triazolo[1,5-c]pyrimidine-2-sulfonamide, a white solid obtained in about 85 percent yield;
$^1$H NMR [300 MHz] (D$_6$-DMSO) ppm: 11.15(s, 1H), 7.70(d, 1H, J=8.0), 7.68(d, 1H, J=7.8), 7.47(dd, 1H, J=8.0, 7.8), 4.68(q, 2H, J=7.0), 3.71(s, 3H), 1.45(t, 3H, J=7.0);

N-(2-chloro-6-methoxycarbonylphenyl)-7-fluoro-5-methoxy[1,2,4]triazolo[1,5-c]pyrimidine-2-sulfonamide, a white solid obtained in over 70 percent yield;
$^1$H NMR [300 MHz] (D$_6$-DMSO) ppm: 11.1(s, 1H), 7.70(d, 1H, J=7.9), 7.68(d, 1H, J=7.9), 7.46(t, 1H, J=7.9), 7.36(s, 1H), 4.23(s, 3H), 3.67(s, 3H);
N-(2-chloro-6-methoxycarbonylphenyl)-8-chloro-5-ethoxy-7-fluoro[1,2,4]triazolo[1,5-c]pyrimidine-2-sulfonamide, a light yellow solid obtained in about 80 percent yield;
$^1$H NMR [300 MHz] (D$_6$-DMSO) ppm: 11.15(s, 1H), 7.71(d, 1H, J=8.0), 7.70(d, 1H, J=7.9), 7.47(dd, 1H, J=8.0, 7.9), 4.68(q, 2H, J=7.1), 3.71(s, 3H), 1.45(t, 3H, J=7.1); and
N-(2-chloro-6-methoxycarbonylphenyl)-7-chloro-5-ethoxy[1,2,4]triazolo[1,5-c]pyrimidine-2-sulfonamide, a light yellow solid obtained in about 82 percent yield;
$^1$H NMR [300 MHz] (D$_6$-DMSO) ppm: 11.0(s, 1H), 7.79(s, 1H), 7.71(d, 1H, J=8.0), 7.68(d, 1H, J=7.9), 7.46(dd, 1H, J=8.0, 7.9), 4.68(q, 2H, J=7.1), 3.69(s, 3H), 1.45(t, 3H, J=7.1).

11. Preparation of N-(2,6-Dichlorophenyl)-7-fluoro-5-ethoxy[1,2,4]triazolo[1,5-c]-pyrimidine-2-sulfonamide Using Unrecovered Sulfilimine Catalyst A first solution containing about 76 mmol of 2-chlorosulfonyl-7-fluoro-5-ethoxy[1,2,4]triazolo[1,5-c]pyrimidine in about 110 g of dichloromethane was prepared by combining 21.8 g of 75 percent purity (about 38 mmol) of bis(5-ethoxy-7-fluoro[1,2,4]triazolo[1,5-c]pyrimidin-2-yl)disulfide, 16.0 g of water, and 190 g of dichloromethane, cooling the mixture to 5° C., and adding 15.1 g (240 mmol) of gaseous chlorine with stirring and cooling over a 75-min period. Another 73.0 g of water was added and the phases were separated. The aqueous phase was extracted with 22.0 g of dichloromethane. The two wet dichloromethane solutions were combined and a total of 118.3 g of water and dichloromethane was removed by azeotropic distillation using a Dean-Stark trap. Another 105.8 g of dichloromethane was added and another 101.5 g of solvents removed by azeotropic distillation. Another about 10 g of dichloromethane was used to facilitate the transfer to a holding vessel. A second solution of 1.35 g (22 mmol) of dimethyl sulfide in 68.2 g of dichloromethane was prepared in a round bottom flask and cooled to about 7° C. Gaseous chlorine (1.5 g, 21 mmol) was added to the vapor space of the flask through a sparge tube with cooling and stirring and, after about 3 min, 15.3 g (94 mmol) of 2,6-dichloroaniline, 19.4 g (160 mmol) of nicotinamide, and 32.2 g of dichloromethane were added with stirring and cooling. After about 30 min, 7.6948 g of 1,4-dichlorobenzene (internal standard for subsequent gas-liquid chromatographic analysis) and then the first prepared solution were added with stirring. The reaction mixture was allowed to warm slowly to ambient temperature and was analyzed by gas-liquid chromatography for the disappearance of the chlorosulfonyl starting material. After 4.5 hours, the mixture was diluted with 42.8 g of water and the resulting slurry was filtered to recover the solids. The solids were reslurried in a mixture of 41.7 g of water and 40.2 g of 2-propanol and rerecovered by filtration and were then reslurried in 13.2 g of 2-propanol and again recovered by filtration. The recovered solids were dried under reduced pressure at 40° C. to obtain 26.9 g of 95 percent purity sulfonamide product (83 percent of theory) as determined by quantitative HPLC using an external standard. There was another 4.8 percent of theory product in the filtrates.

12. Preparation of N-(2,6-Dichlorophenyl)-7,8-dichloro-[1,2,4]triazolo[1.5-c]pyrimidine-2-sulfonamide Using Unrecovered Sulfilimine Catalyst A solution of 0.6 mL (8 mmol) of dimethyl sulfide in 65 mL of dichloromethane was cooled to −20° C. and then 0.4 g (6 mmol) of chlorine was slowly sparged in with stirring and cooling to maintain the temperature below −15° C. A mixture of 5.0 g (31 mmol) of 2,6-dichloroaniline and 6.3 g (49 mmol) of quinoline was then added with cooling and stirring to form a mixture of the sulfilimine catalyst, unreacted 2,6-dichloroaniline, and quinoline. The mixture was allowed to warm to 0° C. and 10 g (45 mmol) of 2-chlorosulfonyl-7,8-dichloro[1,2,4]triazolo[1,5-c]pyrimidine was added with stirring and cooling. The mixture was allowed to warm to about 20° C. and stir for about 16 hours. It was then diluted with 50 mL of methanol and the solids that formed were collected by filtration, washed 2×30 mL with methanol, and dried to obtain 6.2 g (80 percent of theory) of the title compound as a white solid having uv maxima at 210 and 270 nm.

$^1$H NMR [300 MHz] (D$_6$-DMSO) ppm: 8.6(brs, 1H), 7.44(d, 2H, J=8.2), 7.32(dd, 1H, J=8.2), 4.72(q, 2H, J=7.1), 1.50(t, 3H, J=7.1).

The following compounds were prepared similarly using the same sulfilimine catalyst:

N-(2,6-dichlorophenyl)-7-fluoro-5-methoxy[1,2,4]triazolo[1,5-c]pyrimidine-2-sulfonamide, a grey-white solid obtained in about 21 percent yield;

$^1$H NMR [300 MHz] (D$_6$-DMSO) ppm: 8.21(s, 1H), 7.44(d, 2H, J=8.3), 7.33(dd, 1H, J=8.3), 6.98(d, 1H, J=1.1), 4.28(s, 3H);

N-(2,6-dichlorophenyl)-8-chloro-7-fluoro-5-ethoxy[1,2,4]triazolo[1,5-c]pyrimidine-2-sulfonamide, an off-white solid obtained in about 85 percent yield;

$^1$H NMR [300 MHz] (CD$_3$CN) ppm: 7.45(d, 2H, J=8.3), 7.34(dd, 1H, J=8.3), 4.73(q, 2H, J=7.1), 1.51(t, 3H, J=7.1);

N-(2,6-dichlorophenyl)-7-chloro-5-ethoxy[1,2,4]triazolo[1,5-c]pyrimidine-2-sulfonamide, a white solid obtained in about 90 percent yield;

$^1$H NMR [300 MHz] (CD$_3$CN) ppm: 8.29(brs, 1H), 7.47(s, 1H), 7.44(d, 2H, J=8.2), 7.33(dd, 1H, J=8.2), 4.70(q, 2H, J=7.1), 1.51(t, 3H, J=7.1);

N-(2,6-dichlorophenyl)-7-fluoro-5-(1-methylethoxy)[1,2,4]triazolo[1,5-c]pyrimidine-2-sulfonamide, a light yellow-brown solid obtained in about 77 percent yield;

$^1$H NMR [300 MHz] (D$_6$-DMSO) ppm: 7.82(d, 2H, J=8.2), 7.35(d, 1H, J=8.2), 7.32(s, 1H), 5.47(septet, 1H, J=6.1) 1.46(d, 6H, J=6.1); $^{13}$C NMR [75.5 MHz] (D$_6$-DMSO) ppm: 165.9, 161.9 (J$_{C-F}$=242.3), 157.1(J$_{C-F}$=15.2), 150.4, 148.6(J$_{C-F}$=26.0), 135.9, 130.3, 128.7, 86.4(J$_{C-F}$=41.3), 76.6, 21.2.

13. Preparation of N-2-Chlorophenyl-S,S-dimethylsulfilimine and Its Use as a Catalyst in Preparing N-(2-Chlorophenyl)-4-methylbenzenesulfonamide A solution of 12.1 mL (0.17 mol) of dimethyl sulfide in 150 mL of dichloromethane was cooled to −10° C. and then 10.8 g (0.15 mol) of chlorine was slowly sparged in with stirring and cooling to maintain the temperature below −10° C. To this was added 19.1 g (0.15 mol) of 2-chloroaniline and then 38.7 g (0.30 mol) of quinoline with cooling and stirring to form the sulfilimine catalyst. A 105 g aliquot of the 272 g mixture was diluted with 200 mL of dichloromethane and then 25.5 g (0.20 mol) of 2-chloroaniline, 38.7 g (0.30 mol) of quinoline, and, finally, 47.6 g (0.25 mol) of 4-methylbenzenesulfonyl chloride were added with cooling (−10° C.) and stirring. The mixture was allowed to warm to ambient and stir for 2 days. The volatile components were next removed by evaporation under reduced pressure and the oily residue obtained was dissolved in 300 mL of dichloromethane. The resulting solution was washed with 200 mL of 1N aqueous hydrochloric acid and the water wash was back-extracted with 100 mL of dichloromethane. The combined organic phases were dried over magnesium sulfate and concentrated by evaporation under reduced pressure. The residue was dissolved in 175 mL of acetonitrile and reprecipitated by adding 200 mL of water slowly. The solids that formed were collected by filtration, washed with 2-propanol, and dried under reduced pressure to obtain 44.7 g (64 percent of theory) of the title compound as an off-white solid.

$^1$H NMR [300 MHz] (CD$_3$CN) ppm: 9.93(s, 1H), 7.60(d, 2H, J=8.2), 7.37(d, 1H, J=7.4), 7.33(d, 2H, J=8.0), 7.24(m, 2H) 7.16(ddd, 1H, J=7.8, 5.2, 3.7), 2.33(s, 3H); $^{13}$C NMR [75.5 MHz] (D$_6$-DMSO) ppm: 143.1, 137.5, 133.6, 130.1, 129.8, 129.5, 128.8, 127.6, 127.3, 126.9, 126.6, 20.9.

14. Sulfilimine Catalyzed Preparation of N-(2,6-Difluorophenyl)-5-methyl[1,2,4]triazolo[1,5-a]-pyrimidine-2-sulfonamide A solution of 7.0 mL (0.096 mol) of dimethyl sulfide in 70 mL of dichloromethane was cooled to −10° C. and then 5.5 g (0.078 mol) of chlorine was slowly sparged in with stirring and cooling to maintain the temperature below −10° C. To this was added with cooling and stirring 10.0 g (0.078 mol) of 2,6-difluoroaniline and then 50.0 g (0.39 mol) of quinoline to form the sulfilimine catalyst. A 105 g aliquot of the 317 g mixture was diluted with 135 mL of dichloromethane and then 10.0 g (0.078 mol) of 2,6-difluoroaniline and 0.095 mol of 2-chlorosulfonyl-5-methyl[1,2,4]triazolo[1,5-a]pyrimidine were added with stirring and cooling at 0° C. After 20 min, 8.4 g (0.065 mol) of quinoline was added with stirring and the mixture was allowed to warm to ambient temperature overnight. The resulting mixture was filtered to collect the insoluble light brown solid title compound. The filtrate was washed with 150 mL of 1N aqueous hydrochloric acid and the wash water was back-extracted with dichloromethane. The combined organic phases were dried over magnesium sulfate and filtered to remove the magnesium sulfate. The magnesium sulfate was extracted with 50 mL of acetonitrile which was added to the filtrate. The filtrate was concentrated under reduced pressure and the solid residue obtained was slurried in water. The solids were collected by filtration and dried to obtain the title compound. Additional title compound was obtained from the filtrates. In all, 29.8 g of the title compound (87 percent of theory) was obtained as a white solid.

$^1$H NMR [300 MHz] (CD$_3$CN) ppm: 7.71(d, 2H, J=8.7), 7.53(d, 2H, J=8.7), 7.33(tt, 1H, J=8.5, 6.1), 6.98(dd, 2H, J=8.3, 8.2).

15. Sulfilimine Catalyzed Preparation of N-(2-Methoxy-6-(trifluoromethyl)phenyl)-5-ethoxy-7-fluoro[1,2,4]triazolo[1,5-c]pyrimidine-2-sulfonamide A mixture containing about 10 mmol of N-(2-methoxy-6-(trifluoromethyl)phenyl-S,S-dimethylsulfilimine in about 17 mL of dichloromethane solution prepared as in Example 3A omitting the recovery step was diluted with 30 mL of dichloromethane and 10.0 g (52 mmol) of 2-methoxy-6-(trifluoromethyl)aniline, 4.6 g (58 mmol) of pyridine, and 54 mmol of 2-chlorosulfonyl-5-ethoxy-7-fluoro[1,2,4]triazolo[1,5-c]pyrimidine dissolved in 30 mL of dichloromethane were added sequentially with stirring at about −10° C. The mixture was allowed to stir overnight. A small amount of pyridine was added and the mixture was allowed to stir another 6 hours. The volatiles were then removed by evaporation under reduced pressure and the thick slurry remaining was diluted with 30 mL of methanol. The solids present were recovered by filtration, reslurried in methanol, and rerecovered, washed with methanol, and dried. The title compound was obtained as a yellow solid in 63 percent yield (14.9 g).

$^1$H NMR [300 MHz] (CD$_3$CN) ppm: 8.06(s, 1H), 7.47(dd, 1H, J=8.5), 7.31(d, 1H, J=8.1), 7.15(d, 1H, J=8.4), 6.98(d, 1H, J=1.5), 4.73(q, 2H, J=7.1), 3.27(s, 3H), 1.52(t, 3H, J=7.1).

16. Sulfilimine Catalyzed Preparation of N-(2-Chloro-4-(1-methylethoxy)-3-pyridinyl)-5-ethoxy-7-fluoro[1,2,4]triazolo[1,5-c]pyrimidine-2-sulfonamide A mixture containing about 10 mmol of N-(2-chloro-4-(1-methylethoxy)-3-pyridinyl-S,S-dimethylsulfilimine in about 18 mL of dichloromethane solution prepared as in Example 3A omitting the recovery step was diluted with 45 mL of dichloromethane and 4.5 g (24 mmol) of 3-amino-2-chloro-4-(1-methylethoxy)pyridine, 3.2 g (41 mmol) of pyridine, and 36 mmol of 2-chlorosulfonyl-5-ethoxy-7-fluoro[1,2,4]triazolo[1,5-c]pyrimidine dissolved in 19 mL of dichloromethane were added sequentially with stirring and cooling at about –10° C. The mixture was allowed to stir overnight. The volatiles were then removed by evaporation under reduced pressure. The solid residue was dissolved in 1:1 acetonitrile and methanol and 0.5N aqueous hydrochloric acid was added until solids formed. These solids were recovered by filtration, washed 2×75 mL with water, and dried to obtain 11.0 g (73 percent of theory) of the title compound as a white solid. Another 1.7 g (11 percent of theory) of product was obtained from the aqueous phases by extraction.

$^1$H NMR [300 MHz] (CD$_3$CN) ppm: 10.6(s, 1H), 8.16(d, 1H, J=5.8), 7.41(s, 1H), 7.11(d, 1H, J=5.9), 4.71(d, 1H, J=7.0), 4.56(septet, 1H, J=6.0), 1.45(t, 3H, J=7.0), 0.82(d, 6H, J=6.0).

17. Sulfilimine Catalyzed Preparation of N-(5-Bromo-2-pyrimidinyl)-4-methylphenylsulfonamide A mixture containing about 17 mmol of N-5-bromo-2-pyridinyl-S,S-dimethylsulfilimine in about 30 mL of dichloromethane solution prepared as in Example 3A omitting the recovery step was diluted with 43 mL of dichloromethane and then 10.0 g (58 mmol) of 2-amino-5-bromopyridine, 5.5 g (70 mmol) of pyridine, and 14.2 g (74 mmol) of 4-methylbenzenesulfonyl chloride were added sequentially with stirring and cooling at –10° C. The mixture was allowed to warm to 20° C. with stirring. A white precipitate formed quickly. An additional 1.6 g (20 mmol) of pyridine was added and the mixture was allowed to stand for 3 days. Dichloromethane (25 mL) was added to dissolve all the solids and the resulting solution was washed with 150 mL of 0.1N aqueous hydrochloric acid. The aqueous layer was back-extracted with dichloromethane and the combined organic phases were dried over magnesium sulfate and concentrated by evaporation under reduced pressure. The yellow solid residue was recrystallized from 175 mL of acetonitrile and the resulting yellow solid (a first crop of 8.3 g and a second crop of 1.5 g) was recovered to obtain the title compound (41 percent of theory).

$^1$H NMR [300 MHz] (D$_6$-DMSO) ppm: 11.26(S, 1H), 8.26(d, 1H, J=2.4), 7.87(dd, 1H, J=8.8, 2.4), 7.78(d, 2H, J=8.2), 7.34(d, 2H, J=8.1), 7.03(d, 1H, J=8.8), 2.31(s, 3H); $^{13}$C NMR [75.5 MHz] (D$_6$-DMSO) ppm: 150.4, 148.3, 143.4, 140.8, 137.2, 129.5, 127.0, 113.7, 113.2, 20.9.

18. Sulfilimine Catalyzed Preparation of N-(2-Methyl-6-nitrophenyl)-4-chloro-3-nitrophenylsulfonamide A mixture containing about 22 mmol of N-(2-methyl-6-nitrophenyl)-S,S-dimethylsulfilimine in about 25 mL of dichloromethane solution prepared as in Example 3A omitting the recovery step was diluted with 115 mL of dichloromethane and then 11.0 g (72 mmol) of 2-methyl-6-nitroaniline, 15 g (120 mmol) of quinoline, and, 24 g (95 mmol) of 4-chloro-3-nitrobenzenesulfonyl chloride were added sequentially with stirring and cooling at –10° C. The mixture was allowed to warm slowly to 20° C. and stir overnight. An additional 6.0 g (76 mmol) of pyridine was added in two equal portions. After a short time, 100 mL of acetonitrile was added and the resulting solution was washed with 1N aqueous hydrochloric acid. The aqueous phase was extracted with 50 mL of dichloromethane and then 50 mL of acetonitrile. The combined organic phases were dried over magnesium sulfate (washing the magnesium sulfate with 2×50 mL of acetonitrile), and the combined organic solutions were concentrated by evaporation under reduced pressure. The resulting oil was dissolved in warm 2-propanol and reprecipitated by adding 200 mL of 1N aqueous hydrochloric acid. The resulting solids were recovered by filtration, washed with 2-propanol, and dried to obtain 18.5 g (66 percent of theory) of the title compound.

$^1$H NMR [300 MHz] (CD$_3$CN) ppm: 7.71(d, 2H, J=8.7), 7.53(d, 2H, J=8.7), 7.33(tt, 1H, J=8.2, 6.1), 6.98(dd, 2H, J=8.3, 8.2).

19. Sulfilimine Catalyzed Preparation of N-(4-Bromo-1-methyl-5-pyrazolyl)-5-ethoxy-7-fluoro[1,2,4]triazolo[1,5-c]-pyrimidine-2-sulfonamide A mixture containing about 53 mmol of N-(4-bromo-1-methyl-5-pyrazolyl)-S,S-dimethylsulfilimine in about 28 mL of dichloromethane solution prepared in Example 7 omitting the recovery step was cooled to –10° C. and 1.0 g (5.7 mmol) of 5-amino-4-bromo-1-methylpyrazole, 0.54 g (6.8 mmol) of pyridine, 11.8 mmol of 2-chlorosulfonyl-5-ethoxy-7-fluoro[1,2,4]triazolo[1,5-c]pyrimidine, and 5 mL of dichloromethane were added sequentially with stirring and cooling at about –10° C. The mixture was allowed to stir at ambient temperature for 2 days. The solids present were recovered by filtration, washed with a small amount of 2-propanol, and dried to obtain 5.7 g of the title compound as a white solid. A purer sample amounting to 4.6 g (26 percent of theory) was obtained dissolving this in dimethyl sulfoxide and then adding water to reprecipitate it.

$^1$H NMR [300 MHz] (CD$_3$CN) ppm: 10.9(s, 1H), 7.86(s, 1H), 7.36(d, 1H, J=0.72), 4.68(q, 2H, J=7.1), 3.68(s, 3H), 1.46(t, 3H, J=7.1).

20. Sulfilimine Catalyzed Preparation of N-(2,6-Difluorophenyl)-4-chlorobenzenesulfonamide A solution of 7.0 mL (96 mmol) of dimethyl sulfide in 70 mL of dichloromethane was prepared in a round bottom flask and cooled to –10° C. Gaseous chlorine (5.5 g, 78 mmol) was added to the vapor space of the flask through a sparge tube with cooling and stirring. After a short period, 10.0 g (78 mmol) of 2,6-difluoroaniline and then 50 g (390 mmol) of quinoline were added with stirring and cooling. A 109 g aliquot of the 317 g mixture obtained was diluted with 115 mL of dichloromethane and 13.5 g (105 mmol) of 2,6-difluoroaniline and then 27.3 g (125 mmol) of 4-chlorobenzenesulfonyl chloride were added with stirring and cooling to 0° C. The mixture was stirred cold for 1 hour, an additional 8.4 g (65 mmol) of quinoline were added, and the mixture was allowed to warm to ambient temperature and stir overnight. Acetonitrile was added to dissolve the solids present and the resulting solution was washed with 1N aqueous hydrochloric acid. The aqueous phase was extracted with a mixture of 70 mL of dichloromethane and 50 mL of acetonitrile. The organic phases were combined, diluted with 75 mL of acetonitrile, and dried over magnesium sulfate (washing the magnesium sulfate with 2×25 mL of acetonitrile). The combined organics were concentrated by evaporation under reduced pressure. The solid residue was dissolved in 90 percent aqueous methanol and the product precipitated by adding 300 mL of water. The solids were collected by filtration, washed with water, and dried to obtain 30.5 g of the title compound as a light brown solid. Another 4.0 g of title compound was obtained from the filtrate for a total of 34.5 g (87 percent of theory).

$^1$H NMR [300 MHz] (CD$_3$CN) ppm: 7.71(d, 2H, J=8.7), 7.53(d, 2H, J=8.7), 7.33(tt, 1H, J=8.5, 6.1 Hz), 6.98(dd, 2H, J=8.3, 8.2).

What is claimed is:

1. A process for the preparation of an N-arylarylsulfonamide compound of the formula:

Q-SO$_2$NH-AR wherein

Q and AR each independently represents an aromatic hydrocarbyl or aromatic heterocyclyl moiety which comprises combining a sulfonyl chloride compound of the formula:

Q-SO$_2$Cl wherein Q is defined as above
with an amine compound of the formula:

AR-NH$_2$ wherein AR is defined as above
in the presence of an aromatic tertiary amine base and an added catalytic amount of an N-arylsulfilimine compound of the formula:

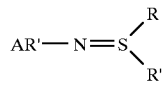

wherein

R represents methyl, ethyl, or n-propyl;

R' represents R, benzyl, or phenyl;

or R and R' together represent tetramethylene; and

AR' represents an aromatic hydrocarbyl or aromatic heterocyclyl moiety.

2. A process according to claim 1 wherein AR' of the N-arylsulfilimine compound is selected to be identical with AR in the amine compound.

3. A process according to claim 1 wherein R and R' each represent methyl.

4. A process according to claim 1 wherein AR represents a substituted phenyl moiety, a substituted pyridinyl moiety, or a substituted pyrazolyl moiety.

5. A process according to claim 4 wherein AR represents an aromatic moiety selected from a) a substituted phenyl moiety of the formula:

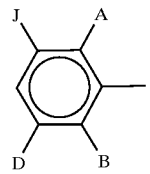

wherein

A represents F, Cl, Br, NO$_2$, CN, C$_1$–C$_4$ fluoroalkyl, CO$_2$(C$_1$–C$_4$ alkyl), CONH(C$_1$–C$_4$ alkyl), CON(C$_1$–C$_4$ alkyl)$_2$, SO$_2$(C$_1$–C$_4$ alkyl), or SO$_2$(C$_1$–C$_4$ fluoroalkyl);

B represents C$_1$–C$_4$ alkyl, F, Cl, Br, O(C$_1$–C$_4$ alkyl), O(C$_1$–C$_4$ fluoroalkyl), S(C$_1$–C$_4$ alkyl), S(C$_1$–C$_4$ fluoroalkyl), N(C$_1$–C$_4$ alkyl)$_2$; or phenyl, phenoxy, or phenylthio each optionally possessing 1 to 3 substituents selected from the group consisting of F, Cl, Br, CN, CF$_3$, NO$_2$, and CH$_3$; and D and J each independently represents H or CH$_3$;

b) a substituted 3-pyridinyl moiety of the formula:

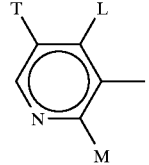

wherein

L and M each independently represents H, C$_1$–C$_4$ alkyl, C$_1$–C$_4$ fluoroalkyl, O(C$_1$–C$_4$ alkyl), O(C$_1$–C$_4$ fluoroalkyl), O(C$_2$–C$_4$ alkoxyalkyl), O(C$_3$–C$_4$ alkenyl), O(C$_3$–C$_4$ alkynyl), S(C$_1$–C$_4$ alkyl), S(C$_1$–C$_4$ fluoroalkyl), SO$_2$(C$_1$–C$_4$ alkyl), SO$_2$(C$_1$–C$_4$ fluoroalkyl), F, C$_1$, Br, I, CN, NO$_2$, C$_6$H$_5$, CO$_2$(C$_1$–C$_4$ alkyl), CO$_2$(C$_3$–C$_4$ alkenyl), CO$_2$(C$_3$–C$_4$ alkynyl), CON(C$_1$–C$_4$ alkyl)$_2$, or CONH(C$_1$–C$_4$ alkyl); and T represents H, F, Cl, Br, I, CH$_3$, or CF$_3$; or c) a 3-, 4-, or 5-pyrazolyl moiety substituted with a C$_1$–C$_3$ alkyl group in the 1-position, with at least one Cl, Br, I, or CF$_3$ and, optionally, with one OCH$_3$ or CH$_3$ group.

6. A process according to claim 5 wherein AR is a substituted phenyl moiety and A represents F, Cl, Br, CF$_3$, NO$_2$, or CO$_2$CH$_3$; B represents F, Cl, Br, CH$_3$, OCH$_3$; D represents H or CH$_3$; and J represents H.

7. A process according to claim 5 wherein AR is a substituted pyridinyl moiety and T represents H and a) M represents Br or Cl and L represents O(C$_1$–C$_3$ alkyl), b) M represents F and L represents C$_1$–C$_2$ alkyl, or c) M represents H and L represents methoxycarbonyl.

8. A process according to claim 5 wherein AR is a substituted pyrazolyl moiety selected from 1-methyl-4-halo-3-pyrazolyl, 1-methyl-4-halo-5-pyrazolyl, and 1-ethyl-3-(trifluoromethyl)-5-(methyl, methoxy, or halo)-4-pyrazolyl.

9. A process according to claim 6 wherein AR is selected from 2,6-dichloro-3-methylphenyl, 2,6-dichlorophenyl, 2,6-difluorophenyl, and 2-methoxycarbonyl-6-chlorophenyl.

10. A process according to claim 1 wherein Q represents a substituted phenyl, substituted pyridinyl, substituted [1,2,4]triazolo[1,5-c]pyrimidine-2-yl, substituted [1,2,4]triazolo[1,5-a]pyrimidine-2-yl, or substituted [1,2,4]triazolo[1,5-a]pyridine-2-yl moiety.

11. A process according to claim 10 wherein the substituents are selected from F, Cl, Br, I, NO$_2$, CN, O(C$_3$–C$_4$ alkenyl), or O($C_3$–$C_4$ alkynyl); $C_1$–$C_4$ alkyl, O($C_1$–$C_4$ alkyl), N($C_1$–$C_4$ alkyl)$_2$, S($C_1$–$C_4$ alkyl), $SO_2$($C_1$–$C_4$ alkyl), $CO_2$($C_1$–$C_4$ alkyl), CONH($C_1$–$C_4$ alkyl), or CON($C_1$–$C_4$ alkyl)$_2$, each alkyl optionally mono to completely substituted with fluorine; or phenyl or phenoxy, each optionally possessing 1 to 3 substituents selected from the group consisting of F, Cl, Br, CN, $CF_3$, $NO_2$, and $CH_3$.

12. A process according to claim 11 wherein the sulfonyl chloride compound is selected from 2-chlorosulfonyl-5-ethoxy-7-fluoro[1,2,4]triazolo[1,5-c]pyrimidine, 2-chlorosulfonyl-5-methoxy-8-fluoro[1,2,4]triazolo[1,5-c]pyrimidine, 2-chlorosulfonyl-5-methoxy-7-methyl[1,2,4]triazolo[1,5-c]pyrimidine, 2-chlorosulfonyl-5-ethoxy-7-methyl[1,2,4]triazolo[1,5-c]pyrimidine, 2-chlorosulfonyl-5-methyl[1,2,4]triazolo[1,5-a]pyrimidine, 2-chlorosulfonyl-5,7-dimethoxy[1,2,4]triazolo[1,5-a]pyrimidine, 2-chlorosulfonyl-5,7-dimethyl[1,2,4]triazolo[1,5-a]pyrimidine, 2-chlorosulfonyl-5-methoxy-7-methyl[1,2,4]triazolo[1,5-a]pyridine, and 2-chlorosulfonyl-5-methoxy-8-chloro[1,2,4]triazolo[1,5-a]pyridine.

13. A process according to claim 3 wherein the catalytic compound is S,S-dimethyl-N-(2,6-dichloro-3-methylphenyl)sulfilimine, S,S-dimethyl-N-(2,6-dichlorophenyl)sulfilimine, S,S-dimethyl-N-(2,6-difluorophenyl)sulfilimine, or S,S-dimethyl-N-(2-methoxycarbonyl-6-chlorophenyl)sulfilimine.

14. A process according to claim 1 wherein the aromatic tertiary amine base is selected from pyridine, a picoline, nicotinamide, and quinoline.

15. A process according to claim 1 wherein the sulfilimine catalyst is prepared essentially immediately before use and is used in the form of the reaction mixture in which it was prepared or in a partially purified form.

16. A process according to claim 1 wherein the temperature is maintained at between about –20 and about 50° C.

17. A process according to claim 1 wherein the amount of catalyst used is between about 2 and about 30 mole percent of the aromatic sulfonyl chloride compound.

18. The method of use of an N-arylsulfilimine compound of the formula:

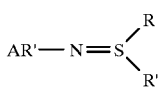

wherein

R represents methyl, ethyl, or n-propyl;

R' represents R, phenyl or benzyl or R and R' together represent tetramethylene; and AR' represents an aromatic hydrocarbyl or aromatic heterocyclyl moiety to catalyze the reaction between an aromatic sulfonyl chloride compound of the formula:

wherein Q represents an aromatic hydrocarbyl or aromatic heterocyclyl moiety with an aromatic amine compound of the formula:

wherein AR represents an aromatic hydrocarbyl or aromatic heterocyclyl moiety to obtain an N-arylarylsulfonamide compound of the formula:

wherein Q and AR are as defined above.

19. A method of use according to claim 18 wherein AR' of the N-arylsulfilimine compound is selected to be identical with AR of the aromatic amine compound.

20. A method of use according to claim 18 wherein R and R' each represent methyl.

* * * * *